United States Patent [19]

Zaiger et al.

[11] Patent Number: Plant 6,283

[45] Date of Patent: Sep. 13, 1988

[54] NECTARINE TREE ("NECTA ZEE")

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 844,352

[22] Filed: Mar. 26, 1986

[51] Int. Cl.[4] ..... A01H 5/03

[52] U.S. Cl. ..... Plt./41

[58] Field of Search ..... Plt./41

*Primary Examiner*—Robert E. Bagwill

[57] ABSTRACT

A new and distinct variety of nectarine tree which has the following unique combination of desirable features.

1. Dwarf size (6 to 8 feet at maturity).
2. Regular and productive bearer.
3. Fruit with attractive red skin color.
4. Fruit with firm flesh and good eating quality.
5. Medium to large freestone fruit.
6. Uniform maturity of fruit.
7. Close leaf nodes with attractive dense foliage.

1 Drawing Sheet

ORIGIN OF THE VARIETY

The new variety of dwarf nectarine was originated by us in the experimental orchard located at Modesto, Calif. It was selected as a second generation seedling from a cross between Early Sun Grand Nectarine (U.S. Plant Pat. No. 1,420) and a dwarf nectarine seedling of unknown parentage which carried the identification of #101 in our breeding program. These seedlings, which were planted and grown under careful observation by us gave many and varying characteristics, including approximately 25% dwarf trees. One such dwarf seedling which is the present variety, having been especially desirable with respect to its fruit was selected for asexual reproduction.

ASEXUAL REPRODUCTION OF THE VARIETY

The new variety of dwarf nectarine tree was asexually reproduced by budding in the experimental orchard located at Modesto, Calif. and shows that all characteristics come true to the original tree in all respects.

SUMMARY OF THE VARIETY

Our new and distinct variety of nectarine tree is of dwarf size (6 to 8 feet at maturity), spreading growth, moderate vigor, and a regular and productive bearer of medium to large, firm, yellow flesh, freestone fruit with a high degree of red skin color. The variety is further characterized by having attractive dense foliage with close leaf nodes and producing large showy pink flowers.

BRIEF DESCRIPTION OF THE PHOTOGRAPHS

The accompanying photographs show typical specimens of the fruit and foliage of our new dwarf nectarine variety. The upper and lower surface of the leaves being illustrated and the exterior and sectional view of the fruit being shown with a stone remaining in place. The photographs were taken shortly after being picked (firm ripe) and the colors are as nearly true as is reasonably possible in a color representation of this type.

DESCRIPTION OF THE VARIETY

The following is a botanical detailed description of our new variety of dwarf nectarine tree, as based on observations of specimens grown at Modesto, Calif., with color terminology in accordance with Reinhold Color Atlas by A. Kornerup and J. H. Wanscher.

Tree:
- *Size.*—Dwarf (6–8 ft. at maturity).
- *Vigor.*—Medium.
- *Form.*—Spreading.
- *Density.*—Dense.
- *Productivity.*—Very productive.
- *Bearer.*—Regular.

Trunk:
- *Size.*—Stocky.
- *Texture.*—Shaggy.
- *Color.*—Grayish brown.

Branches:
- *Size.*—Stocky.
- *Texture.*—Medium rough.
- *Lenticels.*—Large size. Medium number.
- *Color.*—Brown to reddish brown.

Leaves:
- *Size.*—Large. Average length — $7\frac{7}{8}''$. Average width — $1\frac{1}{2}''$.
- *Texture.*—Smooth.
- *Petiole.*—Medium length.
- *Glands.*—Reniform. Number varies from 2 to 4. Average number 2. Located on upper portion of petiole and lower portion of leaf blade.
- *Form.*—Lanceolate.
- *Margin.*—Crenate.
- *Color.*—Upper surface — deep green (28-E-8 to 28-F-7). Lower surface — grayish green (29-E-5 to 29-E-7).

Flower buds:
- *Size.*—Large.
- *Form.*—Plump.
- *Length.*—Medium.

Flower:
- *Blooming period.*—Feb. 28, 1982 to Mar. 10, 1982. Varies slightly due to weather conditions.
- *Size.*—Large, showy.
- *Color.*—Pink.
- *Pollen.*—Present.

Fruit:
- *Maturity when described.*—Firm ripe.
- *Date of first picking.*—June 25, 1982.
- *Date of last picking.*—July 4, 1982.

*Size.*—Medium to large. Average diameter axially — $2\frac{1}{2}''$. Average transversely in suture plane — $2\frac{1}{2}''$.

*Form.*—Globose — nearly symmetrical.

*Suture.*—Shallow, extends from base to apex.

*Ventral surface.*—Slightly lipped, nearly round.

*Cavity.*—Rounded to slightly elongated in surface plane. Average depth — $\frac{1}{2}''$. Average breadth — $\frac{7}{8}''$.

*Apex.*—Varies from very slight point to slight depression. Usually rounded.

Skin:

*Thickness.*—Medium.

*Texture.*—Medium. Tenacious to flesh.

*Down.*—Wanting.

*Tendency to crack.*—None.

*Color.*—Dark yellow ground color (4-A-8 to 5-A-7) overspread with flame red to orange red (7-A-8 to 8-A-8).

Flesh:

*Color.*—Yellow (3-A-8 to 4-A-8).

*Texture.*—Firm.

*Fibers.*—Few — tender.

*Ripens.*—Relatively even — slightly earlier near the apex and suture.

*Juice.*—Moderate.

*Flavor.*—Subacid to mild.

*Aroma.*—Very little.

*Eating quality.*—Good.

Stone:

*Type.*—Freestone. On some fruit, small flesh fragments adhere to some pit cavities.

*Size.*—Large. Average length — $1\frac{5}{8}''$. Average width — $\frac{7}{8}''$. Average thickness — $\frac{3}{4}''$.

*Form.*—Oblong.

*Base.*—Straight to slightly oblique.

*Apex.*—Acute.

*Surface.*—Furrowed to apex, pitted toward base.

*Ridges.*—Rounded toward apex.

*Tendency to split.*—None.

*Color.*—Light brown to brown (6-B-6 to 6-C-7).

Use: Dessert. Home and local market.

Keeping quality: Fair to good.

Shipping quality: Fair to good.

The dwarf nectarine tree and its fruit herein described may vary in slight detail due to climatic, soil conditions and cultural practices under which the variety may be grown; the present description is that of the variety grown under the ecological conditions prevailing at Modesto, Calif.

The following is claimed:

1. A new and distinct variety of nectarine tree which is dwarf in size, (6 to 8 feet at maturity) moderate in vigor, dense, spreading growth and a regular and productive bearer of medium to large, firm, yellow flesh, freestone fruit with a high degree of red skin color, maturing in late June to early July; the tree is further characterized by having attractive dense foliage with close leaf nodes and producing large showy pink flowers.

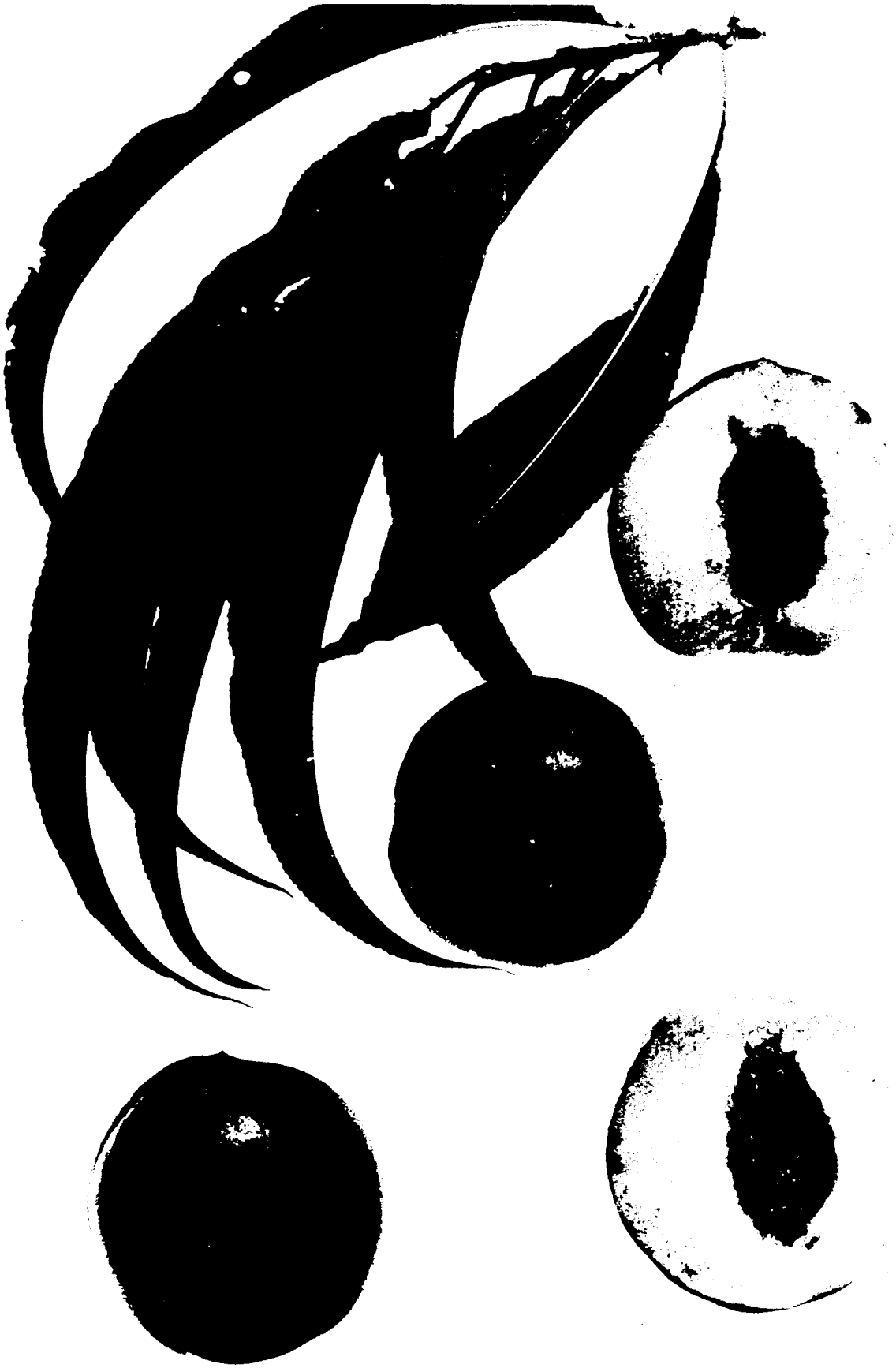

* * * * *